US009456267B2

(12) United States Patent
Matsumoto et al.

(10) Patent No.: US 9,456,267 B2
(45) Date of Patent: Sep. 27, 2016

(54) NOISE REDUCTION APPARATUS AND METHOD, AND PROGRAM

(75) Inventors: Kyosuke Matsumoto, Tokyo (JP); Shiro Suzuki, Kanagawa (JP)

(73) Assignee: Sony Corporation, Tokyo (JP)

( * ) Notice: Subject to any disclaimer, the term of this patent is extended or adjusted under 35 U.S.C. 154(b) by 917 days.

(21) Appl. No.: 13/291,259

(22) Filed: Nov. 8, 2011

(65) Prior Publication Data

US 2012/0163613 A1 Jun. 28, 2012

(30) Foreign Application Priority Data

Dec. 22, 2010 (JP) ................................ P2010-286369

(51) Int. Cl.
*G10K 11/16* (2006.01)
*A61F 11/06* (2006.01)
*H03B 29/00* (2006.01)
*H04R 1/10* (2006.01)
*H04R 3/00* (2006.01)
*G10K 11/178* (2006.01)

(52) U.S. Cl.
CPC .............. *H04R 1/1083* (2013.01); *H04R 3/00* (2013.01); *G10K 11/1786* (2013.01); *G10K 11/1788* (2013.01); *G10K 2210/1081* (2013.01); *G10K 2210/3027* (2013.01); *H04R 2460/01* (2013.01)

(58) Field of Classification Search
CPC ................ G10L 21/0208; G10L 2021/02165; G10K 11/178; G10K 11/1782; G10K 11/1784; G10K 11/1786; G10K 2210/3027; G10K 11/1788; G10K 2210/1081; G10K 2210/3023; H04R 1/1083; H04R 3/00; H04R 3/02; H04R 3/04; H04R 2410/05; H03G 3/32; H03G 9/025; H03G 5/165
USPC ...... 381/71.1, 71.6, 94.1–94.3, 74, 72, 73.1, 381/71.9; 700/94; 181/206
See application file for complete search history.

(56) References Cited

U.S. PATENT DOCUMENTS

| | | | | |
|---|---|---|---|---|
| 5,452,361 | A * | 9/1995 | Jones | 381/71.6 |
| 6,741,707 | B2 * | 5/2004 | Ray | G10K 11/178 381/71.11 |
| 2001/0053229 | A1 * | 12/2001 | Azizi | 381/94.1 |
| 2006/0293882 | A1 * | 12/2006 | Giesbrecht et al. | 704/204 |
| 2008/0159553 | A1 * | 7/2008 | Copley et al. | 381/71.1 |
| 2011/0007907 | A1 * | 1/2011 | Park et al. | 381/71.8 |
| 2011/0158419 | A1 * | 6/2011 | Theverapperuma et al. | 381/71.1 |

FOREIGN PATENT DOCUMENTS

| | | |
|---|---|---|
| JP | 2010-4250 | 1/2010 |

* cited by examiner

*Primary Examiner* — Xu Mei
(74) *Attorney, Agent, or Firm* — Paratus Law Group, PLLC

(57) ABSTRACT

A noise reduction apparatus includes a microphone that picks up a noise from surroundings of a casing, a cancellation signal generating section that generates a cancellation signal for reducing the noise from surroundings, by applying filtering to a signal picked up by the microphone, a predicted signal computing section that computes a predicted signal by predicting a noise from surroundings leaking into the casing, on a basis of the signal picked up by the microphone, an additional-signal control section that generates an additional signal for improving a listening feel of an actual residual noise, on a basis of a predicted residual noise obtained by adding the cancellation signal and the predicted signal, and an addition/output section that adds and outputs the additional signal and the cancellation signal.

5 Claims, 9 Drawing Sheets

NOISE REDUCTION APPARATUS AND METHOD, AND PROGRAM

BACKGROUND

The present disclosure relates to a noise reduction apparatus and method, and a program, and more specifically, the present disclosure relates to a noise reduction apparatus and method, and a program which make it possible to reduce discomfort due to residual noise in noise cancelling.

In related art, noise cancelling headphones have been developed which lower noise level at the listening point by outputting a signal that cancels out noise from the surroundings.

Noise cancelling techniques adopted in noise cancelling headphones currently in practical use fall roughly into two schemes, feedback and feedforward schemes.

Generally, feedback noise cancelling systems have a characteristic that although the band of frequencies over which noise can be cancelled (the band over which noise can be reduced) is narrow, relatively large reduction is possible.

On the other hand, although feedforward noise cancelling systems can reduce noise over a wide band and have stability, there is a conceivable possibility that in the event of disagreement with the assumed transfer function due to factors such as relative position to the noise source, noise increases at the corresponding frequencies.

For this reason, in cases where feedforward noise cancelling systems which can cancel noise over a wide band and have stability are used, there are times when noise becomes conspicuous within a specific narrow band, even though noise is reduced over a wide band. In such cases, the listener (user) is not able to perceive the reduction effect.

As a measure to overcome this problem, there have been also developed techniques that operate also the feedforward scheme simultaneously in addition to the feedback scheme, thereby providing a greater noise reduction effect.

However, in related art, the filter characteristic is constant (fixed filtering scheme) in both the feedback and feedforward schemes, with the noise cancelling characteristic remaining constant even with a change in noise. For this reason, strictly considered, there may be cases where it is not possible to achieve optimum noise cancelling performance for each type of noise. For this reason, use of the adaptive filtering scheme is conceivable as a way to achieve optimum noise cancelling performance for each type of noise.

Accordingly, the applicant has proposed a noise cancelling technique that combines the fixed filtering scheme and the adaptive filtering scheme (see, for example, Japanese Unexamined Patent Application Publication No. 2010-4250).

SUMMARY

However, even if a signal that cancels out noise from the surroundings is outputted using the technique of noise cancelling, it is not possible to completely remove noise from the surroundings due to problems such as a delay in the cancellation process. The noise that remains without being removed completely at this time is referred to as residual noise.

For example, if a residual noise has a steep peak (trough)-like spectral shape, this represents a noise not present in the natural world, which significantly reduces listening comfort for the user. For example, the residual noise can cause the user discomfort such as a sense of oppression or sickness. In particular, when only a specific spectral portion stands out, that is called prominent frequency. It is well recognized that human beings acutely perceive this and complain of discomfort.

Even with use of the technique disclosed in Japanese Unexamined Patent Application Publication No. 2010-4250, for example, it is not possible to reduce such discomfort caused by residual noise.

It is desirable to make it possible to reduce discomfort due to residual noise in noise cancelling.

According to an embodiment of the present disclosure, there is provided a noise reduction apparatus including a microphone that picks up a noise from surroundings of a casing, a cancellation signal generating section that generates a cancellation signal for reducing the noise from surroundings, by applying filtering to a signal picked up by the microphone, a predicted signal computing section that computes a predicted signal by predicting a noise from surroundings leaking into the casing, on a basis of the signal picked up by the microphone, an additional-signal control section that generates an additional signal for improving a listening feel of an actual residual noise, on a basis of a predicted residual noise obtained by adding the cancellation signal and the predicted signal, and an addition/output section that adds and outputs the additional signal and the cancellation signal.

The additional-signal control section may be configured to include a spectral shape computing section that computes a spectral shape of the predicted residual noise, by splitting the predicted residual noise into a plurality of bands of frequencies, and computing a power of each of the split bands, and an additional-signal generating section that generates an additional signal for correcting the computed spectral shape in accordance with a pre-set criterion.

The additional-signal control section may be configured to further include a storing section that stores one or a plurality of spectral shapes of sounds that cause relatively little discomfort to a human being, and a selecting section that selects one spectral shape from among the one or plurality of spectral shapes stored in the storing section, in accordance with the spectral shape computed by the spectral shape computing section, and the additional-signal generating section may be configured to generate the additional signal that brings the spectral shape computed by the spectral shape computing section closer to the selected spectral shape.

According to an embodiment of the present disclosure, there is provided a noise reduction method including picking up a noise from surroundings of a casing, by a microphone, generating a cancellation signal for reducing the noise from surroundings, by applying filtering to a signal picked up by the microphone, by a cancellation signal generating section, computing a predicted signal by predicting a noise from surroundings leaking into the casing, on a basis of the signal picked up by the microphone, by a predicted signal computing section, generating an additional signal for improving a listening feel of an actual residual noise, on a basis of a predicted residual noise obtained by adding the cancellation signal and the predicted signal, by an additional-signal control section, and adding and outputting the additional signal and the cancellation signal, by an addition/output section.

According to an embodiment of the present disclosure, there is provided a program for causing a computer to function as a noise reduction apparatus including a microphone that picks up a noise from surroundings of a casing, a cancellation signal generating section that generates a cancellation signal for reducing the noise from surroundings, by applying filtering to a signal picked up by the microphone, a predicted signal computing section that computes a predicted signal by predicting a noise from surroundings leaking into the casing, on a basis of the signal picked up by the microphone, an additional-signal control section that generates an additional signal for improving a listening feel of an actual residual noise, on a basis of a predicted residual noise obtained by adding the cancellation signal and the predicted signal, and an addition/output section that adds and outputs the additional signal and the cancellation signal.

According to an embodiment of the present disclosure, a cancellation signal for reducing the noise from surroundings is generated by applying filtering to a signal picked up by a microphone, a predicted signal is computed by predicting a noise from surroundings leading into a casing on a basis of the signal picked up by the microphone, an additional signal for improving a listening feel of an actual residual noise is generated on a basis of a predicted residual noise obtained by adding the cancellation signal and the predicted signal, and the additional signal and the cancellation signal are added and outputted.

According to an embodiment of the present disclosure, there is provided a noise reduction apparatus including a microphone that picks up a sound inside a casing, a cancellation signal generating section that generates a cancellation signal for reducing a noise from surroundings, by applying filtering to a signal picked up by the microphone, an additional-signal control section that generates an additional signal for improving a listening feel of a residual noise, on a basis of the signal picked up by the microphone, and an addition/output section that adds and outputs the additional signal and the cancellation signal, after the cancellation signal is outputted.

The additional-signal control section may be configured to include a spectral shape computing section that computes a spectral shape of the signal, by splitting the signal picked up by the microphone into a plurality of bands of frequencies, and computing a power of each of the split bands, and an additional-signal generating section that generates an additional signal for correcting the computed spectral shape in accordance with a pre-set criterion.

The additional-signal control section may be configured to further include a storing section that stores one or a plurality of spectral shapes of sounds that cause relatively little discomfort to a human being, and a selecting section that selects one spectral shape from among the one or plurality of spectral shapes stored in the storing section, in accordance with the spectral shape generated by the spectral shape computing section, and the additional-signal generating section may be configured to generate the additional signal that brings the spectral shape computed by the spectral shape computing section closer to the selected spectral shape.

According to an embodiment of the present disclosure, there is provided a noise reduction method including picking up a sound inside a casing, by a microphone, generating a cancellation signal for reducing a noise from surroundings, by applying filtering to a signal picked up by the microphone, by a cancellation signal generating section, generating an additional signal for improving a listening feel of a residual noise, on a basis of the signal picked up by the microphone, by an additional-signal control section, and adding and outputting the additional signal and the cancellation signal after the cancellation signal is outputted, by an addition/output section.

According to an embodiment of the present disclosure, there is provided a program for causing a computer to function as a noise reduction apparatus including a microphone that picks up a sound inside a casing, a cancellation signal generating section that generates a cancellation signal for reducing a noise from surroundings, by applying filtering to a signal picked up by the microphone, an additional-signal control section that generates an additional signal for improving a listening feel of a residual noise, on a basis of the signal picked up by the microphone, and an addition/output section that adds and outputs the additional signal and the cancellation signal, after the cancellation signal is outputted.

According to an embodiment of the present disclosure, a cancellation signal for reducing a noise from surroundings is generated by applying filtering to a signal picked up by a microphone, an additional signal for improving a listening feel of a residual noise is generated on a basis of the signal picked up by the microphone, and the additional signal and the cancellation signal are added and outputted after the cancellation signal is outputted.

DETAILED DESCRIPTION OF EMBODIMENTS

Hereinbelow, embodiments of the present disclosure will be described with reference to the drawings.

Figure 1:
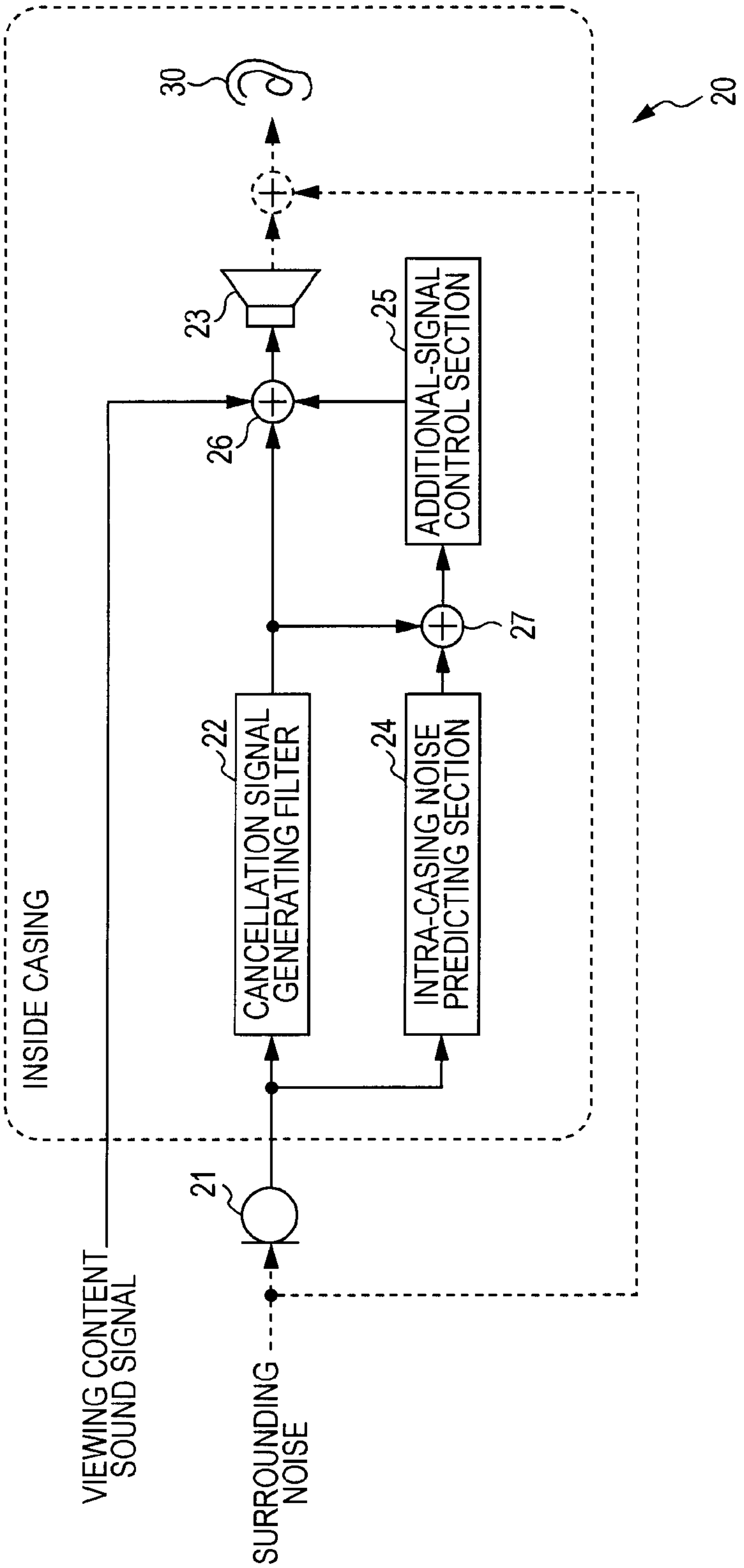
FIG. 1 is a block diagram showing an example of the configuration of a noise reduction apparatus according to an embodiment of the present disclosure.

FIG. 1 is a block diagram showing an example of the configuration of a noise reduction apparatus according to an embodiment of the present disclosure. A noise reduction apparatus 20 shown in the drawing is configured as, for example, an FF-type noise cancelling headphone.

It should be noted that an FF (Feedforward)-type noise cancelling headphone is a type of noise cancelling headphone that picks up noise from the surroundings using a microphone provided outside the casing of the headphone. That is, an FF-type noise cancelling headphone is aimed at reducing noise by applying appropriate filtering to the noise picked up by the microphone located outside the casing, and returning the anti-phase component of the noise signal.

As shown in the drawing, the noise reduction apparatus 20 is provided with a microphone 21, a cancellation signal generating filter 22, a speaker 23, an intra-casing noise predicting section 24, an additional-signal control section 25, an adder 26, and an adder 27.

In FIG. 1, the sound signal of viewing content (viewing content sound signal) outputted from a content playback section (not shown) is supplied to the adder 26, and is added with an additional signal generated by the additional-signal control section 25 described later before being outputted from the speaker 23.

The microphone 21 is configured to, for example, pick up noise from the surroundings of the headphone, and output the picked up noise to the cancellation signal generating filter 22 and the intra-casing noise predicting section 24.

The cancellation signal generating filter 22 applies filtering to the sound signal outputted from the microphone 21 to thereby generate such a cancellation signal that reduces noise from the surroundings. It should be noted that the filter provided in the cancellation signal generating filter 22 may be configured as a fixed filter whose filter characteristic is constant, or may be configured as an adaptive filter whose filter characteristic varies adaptively.

The intra-casing noise predicting section 24 is configured to predict a noise from the surroundings which will leak into the casing, and output the predicted noise.

Even if a signal that reduces noise from the surroundings is outputted using the technique of noise cancelling, it is not possible to completely remove noise from the surroundings. That is, residual noise is present. The corresponding signal is obtained by adding the signal outputted from the cancellation signal generating filter 22, and the signal outputted from the intra-casing noise predicting section 24 by the adder 27. This is referred to as predicted residual noise.

That is, the signal outputted from the adder 27 is a signal corresponding to a noise that is present even after the surrounding noise (predicted to be) leaking into the casing is added with a signal for removing the noise.

The additional-signal control section 25 is configured to generate and output an additional signal used for purposes such as improving the listening feel of the actual residual noise and reducing discomfort, on the basis of the predicted residual noise outputted from the adder 27.

The sound outputted from the speaker 23 is a signal obtained by adding the output from the cancellation signal generating filter 22, and the output from the additional-signal control section 25 by the adder 26. This signal is acoustically superposed onto the noise from the surroundings leaking into the casing, before reaching an ear 30 of the user.

It should be noted that in the configuration shown in FIG. 1, the portion made up of the microphone 21, the cancellation signal generating filter 22, the speaker 23, and the adder 26 can be configured in the same manner as that of noise cancelling headphones of related art.

Figure 2:
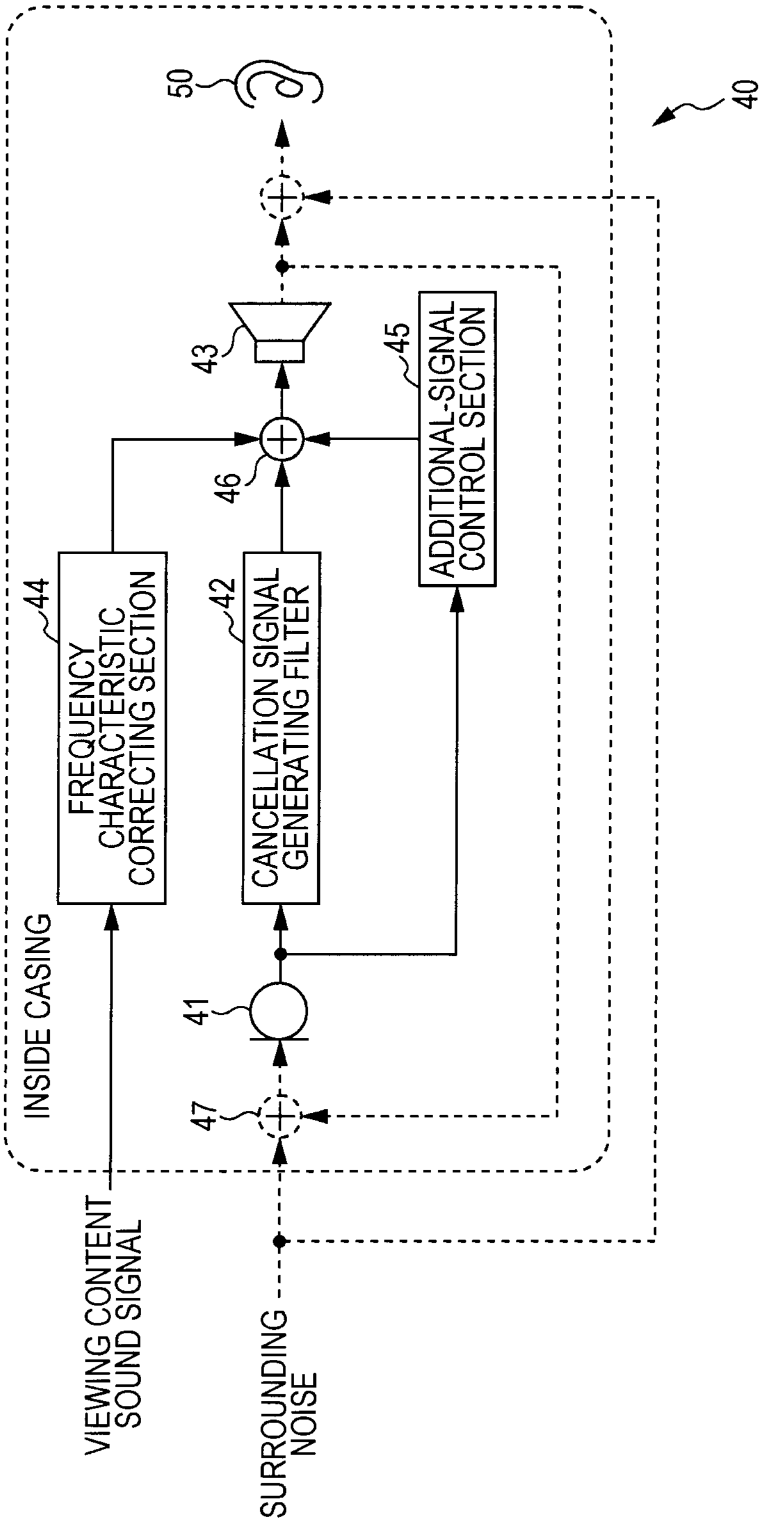
FIG. 2 is a block diagram showing another example of the configuration of a noise reduction apparatus according to an embodiment of the present disclosure.

FIG. 2 is a block diagram showing another example of the configuration of a noise reduction apparatus according to an embodiment of the present disclosure. A noise reduction apparatus 41 shown in the drawing is configured as, for example, an FB-type noise cancelling headphone.

It should be noted that an FB (Feedback)-type noise cancelling headphone is generally a type of noise cancelling headphone that picks up noise from the surroundings using a microphone provided inside the casing of the headphone (near the user's ear). That is, an FB-type noise cancelling headphone attenuates noise entering the casing of the headphone from the outside, by returning the anti-phase component of the noise signal picked up by the microphone.

As shown in the drawing, the noise reduction apparatus 40 is provided with a microphone 41, a cancellation signal generating filter 42, a speaker 43, a frequency characteristic correcting section 44, an additional-signal control section 45, and an adder 46. An adder 47 indicates that the sound outputted from the speaker 43 is acoustically fed back to the microphone.

In FIG. 2, the sound signal of viewing content (viewing content sound signal) outputted from a content playback section (not shown) is supplied to the frequency characteristic correcting section 44. By taking into account the fact that the viewing content sound signal is suppressed by a signal generated by the cancellation signal generating filter 42 described later, the frequency characteristic correcting section 44 is configured to perform such a frequency characteristic correction that compensates for the suppression effect.

The microphone 41 is configured to, for example, pick up the sound of noise from the surroundings of the headphone leaking into the casing, and the sound outputted from the speaker 43, and output each of the picked up sounds to the cancellation signal generating filter 42 and the additional-signal control section 45.

The cancellation signal generating filter 42 applies filtering to the sound signal outputted from the microphone 41 to thereby generate such a cancellation signal that reduces noise from the surroundings. It should be noted that the filter provided in the cancellation signal generating filter 42 may be configured as a fixed filter whose filter characteristic is constant, or may be configured as an adaptive filter whose filter characteristic varies adaptively.

The additional-signal control section 45 is configured to generate and output an additional signal used for purposes such as improving the listening feel of residual noise and reducing discomfort, on the basis of the signal outputted from the microphone 41. Since the microphone 41 picks up the sound inside the casing of the headphone in the configuration shown in FIG. 2, a signal containing residual noise is outputted from the microphone 41.

The adder 46 adds the signals outputted from the frequency characteristic correcting section 44, the cancellation signal generating filter 42, and the additional-signal control section 45, and outputs the result to the speaker 43.

The sound outputted from the speaker 43 is acoustically superposed onto the noise from the surroundings leaking into the casing, before reaching an ear 50 of the user.

It should be noted that in the configuration shown in FIG. 2, the portion made up of the microphone 41, the cancellation signal generating filter 42, the speaker 43, the frequency characteristic correcting section 44, the adder 46, and the adder 47 can be configured in the same manner as that of noise cancelling headphones of related art.

Figure 3:
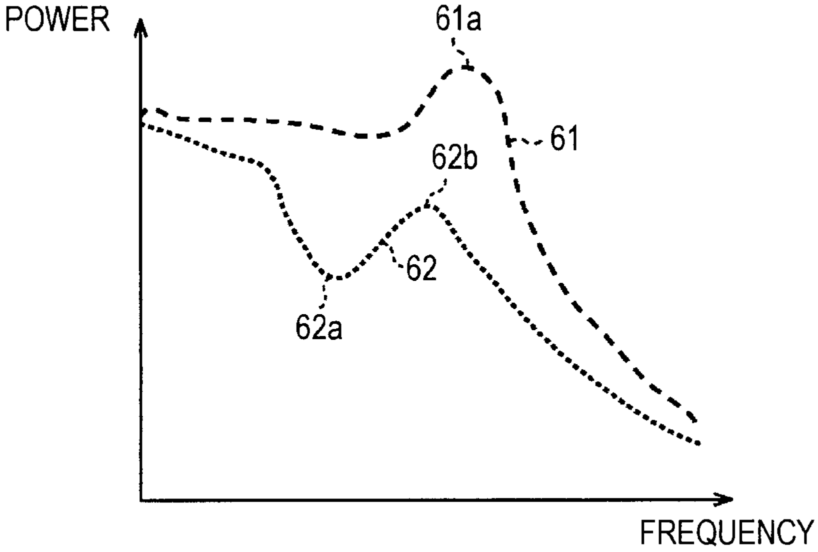
FIG. 3 is a diagram explaining the power spectrum of each signal.
Figure 4:
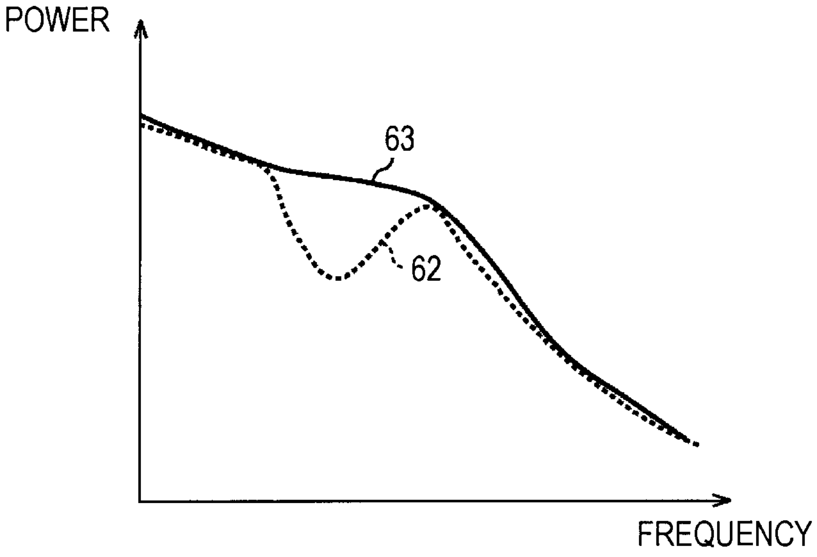
FIG. 4 is a diagram explaining the power spectrum of each signal.
Figure 5:
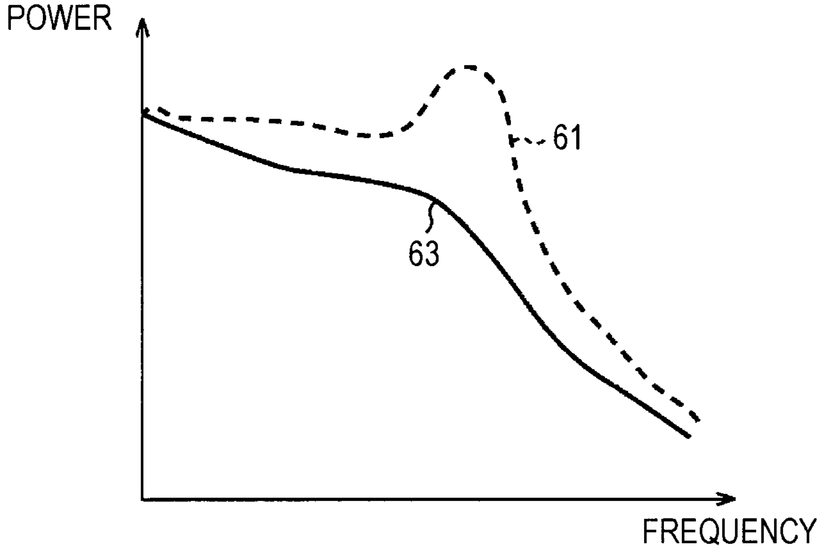
FIG. 5 is a diagram explaining the power spectrum of each signal.

Next, the additional signal generated by the additional-signal control section 25 or the additional-signal control section 45 will be described with reference to FIGS. 3 to 5. In FIGS. 3 to 5, the horizontal axis represents frequency, and the vertical axis represents the power of each frequency component. The power spectrum of each signal is indicated by a dotted line or solid line in the drawings.

A dotted line 61 shown in FIG. 3 indicates the power spectral density of a signal obtained by adding the noise from the surrounding leaking into the casing of the headphone to the sound signal of viewing content. That is, the dotted line 61 indicates an example of the frequency spectrum of a sound as heard by the user's ear inside the headphone in the state where processing associated with removal of noise (noise cancelling) is not performed.

A dotted line 62 shown in FIG. 3 indicates the frequency spectral density of a signal generated by the noise cancelling headphone of related art. For example, the dotted line 62 indicates an example of the frequency spectral density of a sound as heard by the user's ear inside the headphone in the state where the additional-signal control section 45 shown in FIG. 2 is not operated.

That is, the dotted line 62 indicates the frequency spectral density of a signal obtained by applying processing associated with noise cancelling of related art to the signal corresponding to the dotted line 61.

As shown in FIG. 3, the dotted line 61 forms a steep peak-like shape in a portion 61*a*. The frequency component corresponding to the portion 61*a* becomes so-called prominent frequency, which is easily perceived by the user. In contrast, in the dotted line 62 representing a signal to which processing associated with noise cancelling has been applied, the frequency component corresponding to the portion 61*a* is reduced. However, the dotted line 62 has a steep peak-like shape in a portion 62*b*. The frequency component corresponding to the portion 62*b* becomes so-called prominent frequency, which is easily perceived by the user. Such a noise causes discomfort to the user. In this way, discomfort due to residual noise occurs.

Accordingly, the additional-signal control section 45 generates a signal necessary for generating a solid line 63 shown in FIG. 4.

The solid line 63 shown in FIG. 4 indicates, for example, the power spectrum of a sound as heard by the user's ear on which a headphone configured as the noise reduction apparatus 40 in FIG. 2 is mounted. In the present case, of course, this means the sound as heard by the user's ear inside the headphone in the state where the additional-signal control section 45 in FIG. 2 is operated. Like the dotted line 62 in FIG. 3, the dotted line 62 shown in FIG. 4 indicates the power spectral of a sound reaching the user's ear when processing associated with noise cancellation is performed in the noise cancelling headphone of related art.

As shown in FIG. 4, unlike the dotted line 62, the solid line 63 has a shape that gently slopes down from the left to right in the drawing, with no steep peak-shaped and trough-shaped portions. That is, the signal corresponding to the solid line 63 has no prominent frequency component, and hence is unlikely to cause discomfort to the listener.

Like the solid line 63 in FIG. 4, the solid line 63 shown in FIG. 5 indicates, for example, the power spectrum of a sound as heard by the user's ear on which a headphone configured as the noise reduction apparatus 40 shown in FIG. 2 is mounted. Like the dotted line 61 in FIG. 3, the dotted line shown in FIG. 5 indicates the power spectral density of a signal obtained by adding the noise from the surrounding leaking into the casing of the headphone to the sound signal of viewing content. That is, the dotted line 61 indicates an example of the frequency spectrum of a sound as heard by the user's ear inside the headphone in the state where processing associated with removal of noise (noise cancelling) is not performed.

As shown in FIG. 5, the shape of the solid line 63 exhibits generally small power in comparison to the shape of the dotted line 61. Also, the solid line 63 has a shape that gently slopes down from the left to right in the drawing, with no steep peaks and troughs. That is, since no prominent frequency component is present in the signal corresponding to the solid line 63, discomfort is reduced in comparison to the sound represented by the dotted line 61.

In this way, if the signal as indicated by the solid line 63 in FIG. 4 or 5 can be generated, it is possible to reduce discomfort due to residual noise, while attaining the surrounding noise reduction effect.

While the foregoing description about FIGS. 3 to 5 is given with the case of noise cancelling by the noise reduction apparatus 40 in FIG. 2 as an example, the same applies to the noise reduction apparatus 20 in FIG. 1.

It should be noted, however, that in the case of the configuration in FIG. 1, the dotted line 61 in FIG. 3 or 5 indicates the power spectrum of a sound corresponding to the signal outputted from the microphone 21, and the dotted line 62 in FIG. 3 or 4 indicates the power spectrum of a sound corresponding to the signal outputted from the adder 27. That is, in the case of the configuration in FIG. 1, in actuality, the additional-signal control section 25 performs control associated with to an additional signal without taking the sound signal of viewing content into consideration.

It is considered more desirable to, for example, generate an additional signal in the manner as described with reference to FIGS. 3 to 5 by analyzing a sound that is as close as possible to the sound reaching the ear 50 of the user as in the case of the noise reduction apparatus 40 in FIG. 2, because it is possible to reduce discomfort more effectively. However, it is considered that even if an additional signal is generated by analyzing only a predicted residual noise (signal outputted from the adder 27) as in the case of the noise reduction apparatus 20 in FIG. 1, discomfort caused by the sound reaching the ear 30 of the user can be sufficiently reduced.

Next, a description will be given of a detailed example of the configuration of the additional-signal control section 25 or the additional-signal control section 45.

Figure 6:
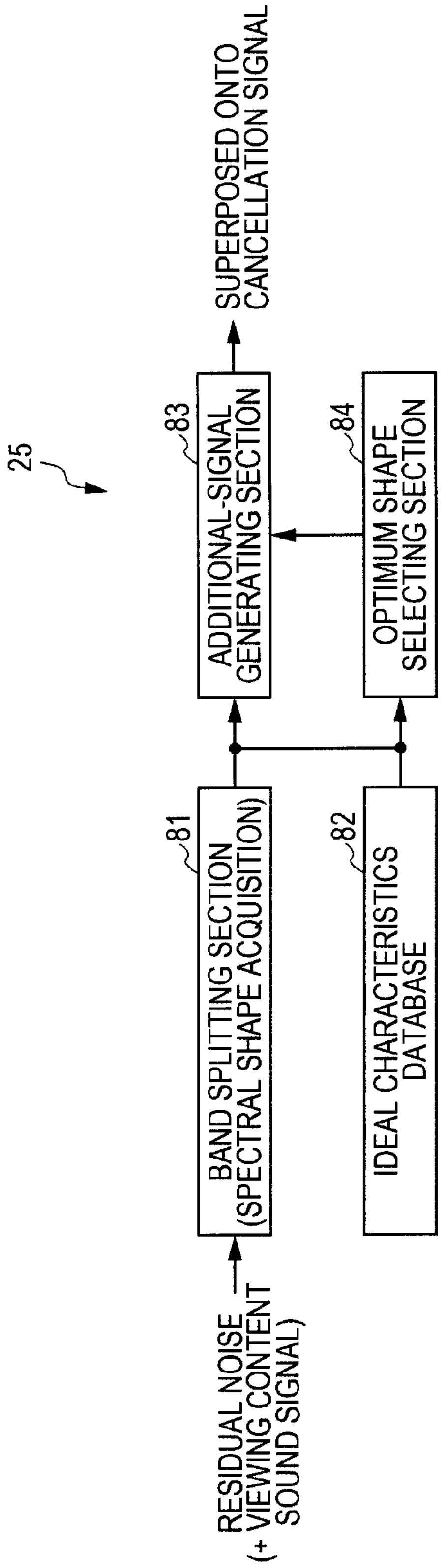
FIG. 6 is a block diagram showing a detailed example of the configuration of an additional-signal control section.

FIG. 6 is a block diagram showing a detailed example of the configuration of the additional-signal control section 25 (or the additional-signal control section 45).

In the drawing, a band splitting section 81 is configured to split an inputted signal into bands, and generate the spectrum of each of the split bands. This produces, for example, the spectral shape as indicated by the dotted line 62 in FIG. 3 or 4.

An ideal characteristics database 82 stores, for example, spectral shapes with which to perform modification using an additional signal. The ideal characteristics database 82 stores, for example, a plurality of spectral shapes representing samples of sounds that do not have steep peak-shaped or trough-shaped portions and hence cause little discomfort. That is, the ideal characteristics database 82 stores, for example, the spectral shapes of sounds that cause relatively little discomfort to human beings.

For example, the ideal characteristics database 82 stores one or a plurality of samples of spectral shapes, such as a spectral shape in which power decreases gently from low to high frequencies, or a spectral shape which has a flat characteristic at low frequencies and in which power decreases gently from medium to high frequencies.

An optimum shape selecting section 84 selects an optimum spectral shape from among the samples of spectral shapes stored in the ideal characteristics database 82, on the basis of the spectral shape obtained by processing in the band splitting section 81. That is, a spectral shape that is regarded as closest to the spectral shape obtained by processing in the band splitting section 81 is selected.

For example, in the case where the spectral shape as indicated by the dotted line 62 in FIG. 3 or 4 is obtained by processing in the band splitting section 81, a spectral shape in which power decreases gently from low to high frequencies is selected.

It should be noted that an optimum spectral shape may be selected on the basis of, for example, the sum of squared differences between the power spectra in each band of the spectral shape obtained by processing in the band splitting section 81, and each of the spectral shapes stored in the ideal characteristics database 82, or may be selected by other methods.

Alternatively, only a single pre-set spectral shape may be stored in the ideal characteristics database 82.

An additional-signal generating section 83 generates an additional signal necessary to bring the spectral shape obtained by processing in the band splitting section 81 closer to the spectral shape selected by the optimum shape selecting section 84.

The additional-signal generating section 83 computes, for example, a spectral shape that minimizes the inter-spectral distance D(T, X) represented by Equation (1), as an ideal spectral shape.

$$D(T, X) = \sum_{i=0}^{N} |sT(i) - X(i)|^2 \tag{1}$$

In Equation (1), T(i) denotes the spectral density in each band of the spectral shape selected by the optimum shape selecting section 84, and X(i) denotes the spectral density in each band of the spectral shape obtained by processing in the band splitting section 81. Also, "i" denotes the index of each split band, and "s" denotes a scaling factor by which to multiply T(i).

Here, the scaling factor "s" can be calculated by Equation (2), for example. That is, the largest of the values of X(i)/T(i) in individual split bands is calculated as the scaling factor "s".

$$s = \max_i X(i)/T(i) \tag{2}$$

Figure 7:
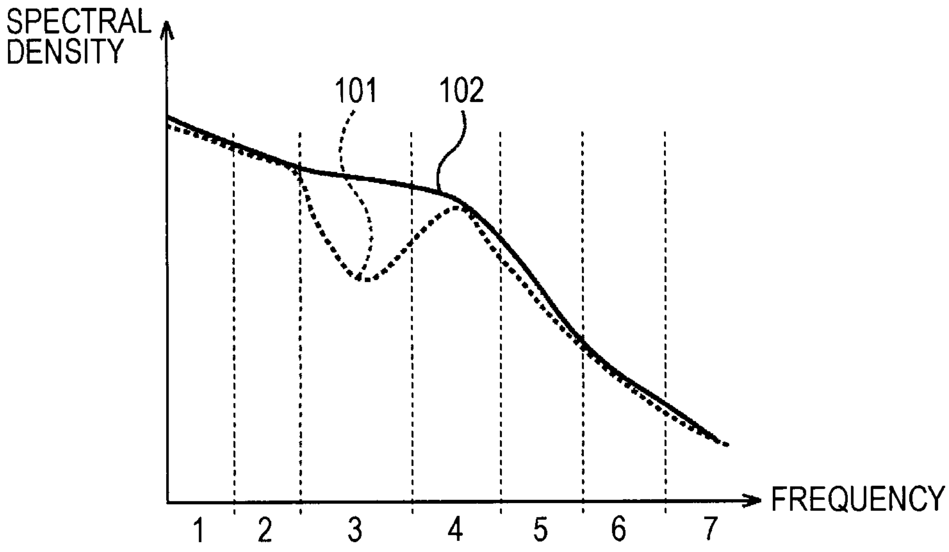
FIG. 7 is a diagram explaining about generation of an additional signal.

For example, suppose that the spectral shape indicated by a dotted line 101 shown in FIG. 7 is obtained as the spectral shape obtained by processing in the band splitting section 81. At this time, for example, the spectral shape indicated by a solid line 102 shown in FIG. 7 is computed as an ideal spectral shape. It should be noted that in FIG. 7, the horizontal axis and the vertical axis respectively represent frequency and spectral density, the spectrum of each signal is indicated by a dotted line or solid line in the drawing, and the numerical values presented along the horizontal axis denote the indices of split bands.

The additional-signal generating section 83 generates a signal for each split band so as to fill up the difference between the spectral shape obtained by processing in the band splitting section 81 and the ideal spectral shape calculated by Equation (1) (bring the difference in spectral density to zero), and sets this as an additional signal. For example, an additional signal is generated by processing a signal such as white noise so as to be outputted at a predetermined volume in each split band. Alternatively, instead of white noise or the like, an environmental sound (such as the sound of ripples) that is generally considered pleasant may be used, or in the configuration shown in FIG. 1, a part of the frequency band of the noise from the surroundings picked up by the microphone may be used.

For example, an additional signal is outputted in such a way that white noise in the third split band of frequencies in FIG. 7 is outputted at a large volume, and white noise in each of the fourth to sixth split bands of frequencies is outputted at a small volume.

That is, the additional-signal generating section 83 generates an additional signal for correcting the spectral shape obtained by processing in the band splitting section 81 so as to become closer to the ideal spectral shape.

As the additional signal generated in this way is added at the adder 26 or the adder 46, for example, as described above with reference to FIGS. 4 and 5, noise from the surroundings can be reduced, and also discomfort due to residual noise can be reduced.

While the foregoing description is directed to the case of generating an additional signal in such a way as to fill up the difference between the spectral shape obtained by processing in the band splitting section 81 and the ideal spectral shape calculated by Equation (1), an additional signal may be generated by other methods.

For example, an additional signal may be generated in such a way as to attain a spectral shape in which spectral density in the higher band does not exceed spectral density in the lower band at all times. This is because a signal having a spectral shape with no steep peak-shaped or trough-shaped portions is obtained in this way. That is, an additional signal may be generated in such a way as to correct the spectral shape obtained by processing in the band splitting section 81 in accordance with a pre-set criterion (for example, spectral density in the higher band does not exceed spectral density in the lower band at all times), for example.

Figure 8:
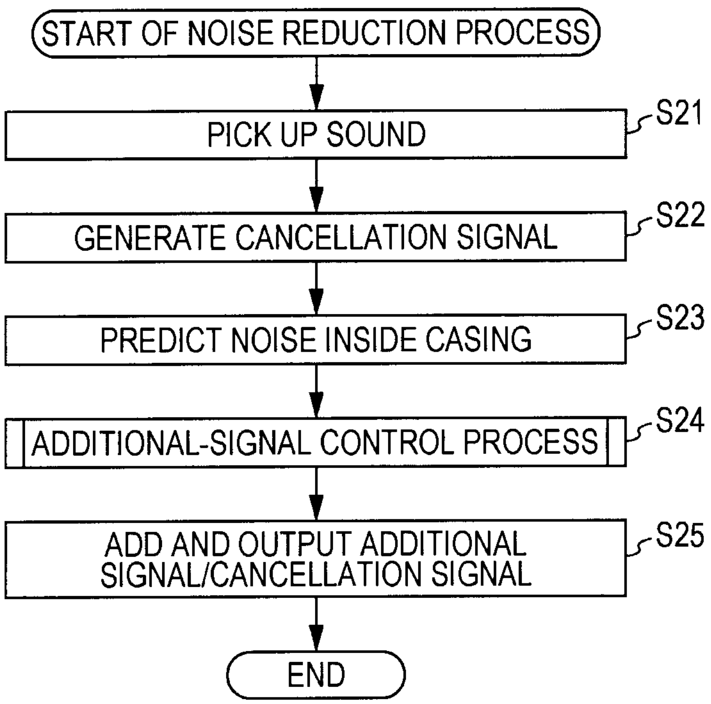
FIG. 8 is a flowchart explaining an example of a noise reduction process.

Next, referring to the flowchart in FIG. 8, an example of a noise reduction process by the noise reduction apparatus 20 in FIG. 1 will be described.

In step S21, the microphone 21 picks up noise from the surroundings of the headphone, for example. The sound signal of the noise picked up at this time is outputted to the cancellation signal generating filter 22, and the intra-casing noise predicting section 24.

In step S22, in accordance with the process in step S21, the cancellation signal generating filter 22 applies filtering to the sound signal outputted from the microphone 21, thereby generating such a cancellation signal that reduces noise from the surroundings.

In step S23, the intra-casing noise predicting section 24 predicts a noise from the surroundings leaking into the casing, and generates a signal corresponding to the predicted noise.

In step S24, the additional-signal control section 25 executes an additional-signal control process, on the basis of a signal obtained by adding the signal generated by the process of step S22, and the signal generated by the process of step S23.

In step S25, the additional signal generated by the process of step S24 is added to the cancellation signal and the sound signal of viewing content by the adder 26, and outputted.

Figure 10:
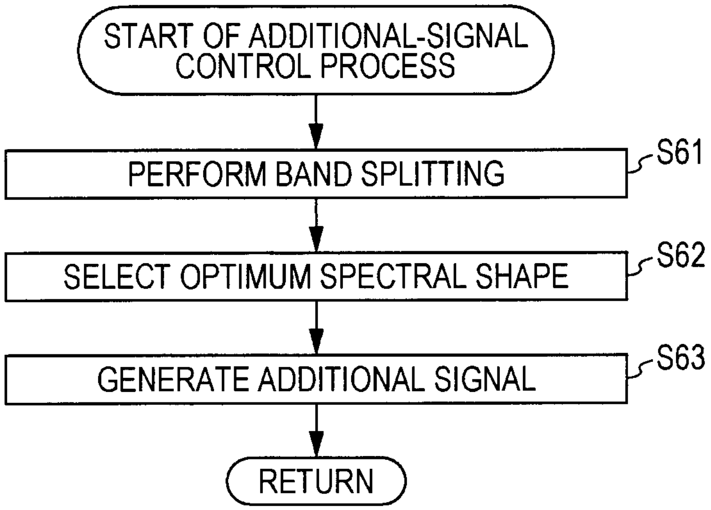
FIG. 10 is a flowchart explaining an example of an additional-signal control process.

It should be noted that a detailed example of the additional-signal control process will be described later with reference to the flowchart in FIG. 10.

The noise reduction process is executed in this way.

Figure 9:
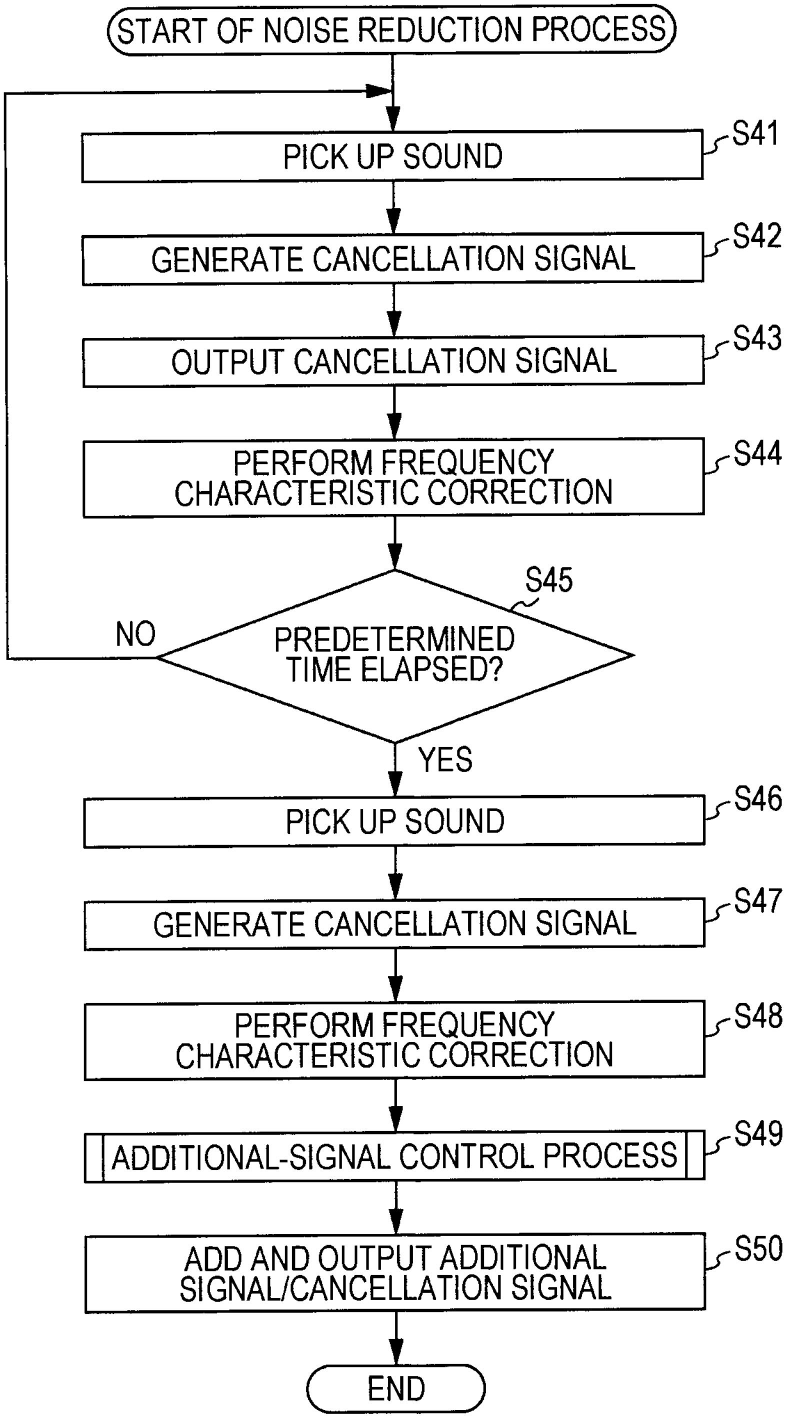
FIG. 9 is a flowchart explaining another example of a noise reduction process.

Next, referring to the flowchart in FIG. 9, an example of a noise reduction process by the noise reduction apparatus 40 in FIG. 2 will be described.

In step S41, the microphone 41 picks up, for example, the sound of noise from the surroundings of the headphone leaking into the casing, and the sound outputted from the speaker 43. The sound signal of each of the sounds picked up at this time is outputted to the cancellation signal generating filter 42 and the additional-signal control section 45.

In step S42, the cancellation signal generating filter 42 applies filtering to the sound signal outputted from the microphone 41 to thereby generate such a cancellation signal that reduces noise from the surroundings.

In step S43, the cancellation signal generated by the process of step S42 is outputted.

In step S44, by taking into account the fact that the viewing content sound signal is suppressed by the signal generated by the process of step S42, the frequency characteristic correcting section 44 performs such a frequency characteristic correction that compensates for the suppression effect.

In step S45, it is determined whether or not a predetermined time has elapsed. If it is determined that a predetermined time has not elapsed, the processing returns to step S41, and the subsequent processing is repeatedly executed.

The sound picked up immediately after activation of the noise reduction apparatus 40 in FIG. 2 does not reflect the effect of noise cancellation. If an additional signal is added in this state, there is a possibility that the noise reduction apparatus 40 does not operate as expected. Thus, in step S45, the processing is put on standby until a predetermined time elapses.

If it is determined in step S45 that a predetermined time has elapsed, the processing proceeds to step S46.

In step S46, the microphone 41 picks up, for example, the sound of noise from the surroundings of the headphone leaking into the casing, and the sound outputted from the speaker 43. The sound signal of each of the sounds picked up at this time is outputted to the cancellation signal generating filter 42 and the additional-signal control section 45.

In step S47, the cancellation signal generating filter 42 applies filtering to the sound signal outputted from the microphone 41 to thereby generate such a cancellation signal that reduces noise from the surroundings.

In step S48, by taking into account the fact that the viewing content sound signal is suppressed by the signal generated by the process of step S47, the frequency characteristic correcting section 44 performs such a frequency characteristic correction that compensates for the suppression effect.

In step S49, the additional-signal control section 45 executes an additional-signal control process on the basis of the signal that is outputted from the microphone 41 by the process of step S46.

In step S50, the additional signal generated by the process of step S49 is added to the cancellation signal and the sound signal of viewing content by the adder 46, and outputted.

It should be noted that a detailed example of the additional-signal control process will be described later with reference to the flowchart in FIG. 10.

The noise reduction process is executed in this way.

Next, referring to the flowchart in FIG. 10, a detailed example of the additional-signal control process in step S24 in FIG. 8, or step S49 in FIG. 9 will be described.

In step S61, the band splitting section 81 splits an inputted signal into bands, and generates the spectrum of each of the split bands. This produces, for example, the spectral shape as indicated by the dotted line 62 in FIG. 3 or 4.

In step S62, the optimum shape selecting section 84 selects an optimum spectral shape from among the samples of spectral shapes stored in the ideal characteristics database 82, on the basis of the spectral shape obtained in accordance with the process of step S61. That is, a sample of spectral shape that is regarded as closest to the spectral shape obtained by processing in the band splitting section 81, and a scaling factor by which to multiply the corresponding spectral shape are selected. Thus, the ideal spectral shape described above is generated.

At this time, the ideal spectral shape is computed by multiplying each band of the selected sample of spectral shape by the selected scaling factor.

In step S63, the additional-signal generating section 83 generates an additional signal on the basis of the spectral shape obtained in accordance with the process of step S61, and the ideal spectral shape obtained in accordance with the process of step S62. At this time, the additional-signal generating section 83 generates a signal for each split band so as to fill up the difference between the spectral shape obtained in accordance with the process of step S61 and the ideal spectral shape obtained in accordance with the process of step S62 (bring the difference in spectral density to zero), and sets this as an additional signal.

In this way, noise from the surroundings can be reduced, and also discomfort due to residual noise can be reduced.

While the foregoing description is directed to the case in which the sound signal of viewing content is added by the adder 26 in the noise reduction apparatus 20 in FIG. 1, the sound signal of viewing content may not be added. That is, the noise reduction apparatus 20 in FIG. 1 may not necessarily be used for listening to content, but may be used simply for reducing noise from the surroundings.

Also, while the foregoing description is directed to the case in which the sound signal of viewing content is added by the adder 46 in the noise reduction apparatus 40 in FIG. 2, the sound signal of viewing content may not be added. That is, the noise reduction apparatus 40 in FIG. 2 may not necessarily be used for listening to content, but may be used simply for reducing noise from the surroundings.

It should be noted that the series of processes described above can be executed by both of hardware and software. If the series of processes described above is to be executed by software, a program constituting the software is installed into a computer embedded in dedicated hardware from a network or a recording medium. Also, the program is installed into, for example, a general-purpose personal computer 700 as shown in FIG. 11 that can execute various kinds of functions when installed with various kinds of programs, from a network or a recording medium.

Figure 11:
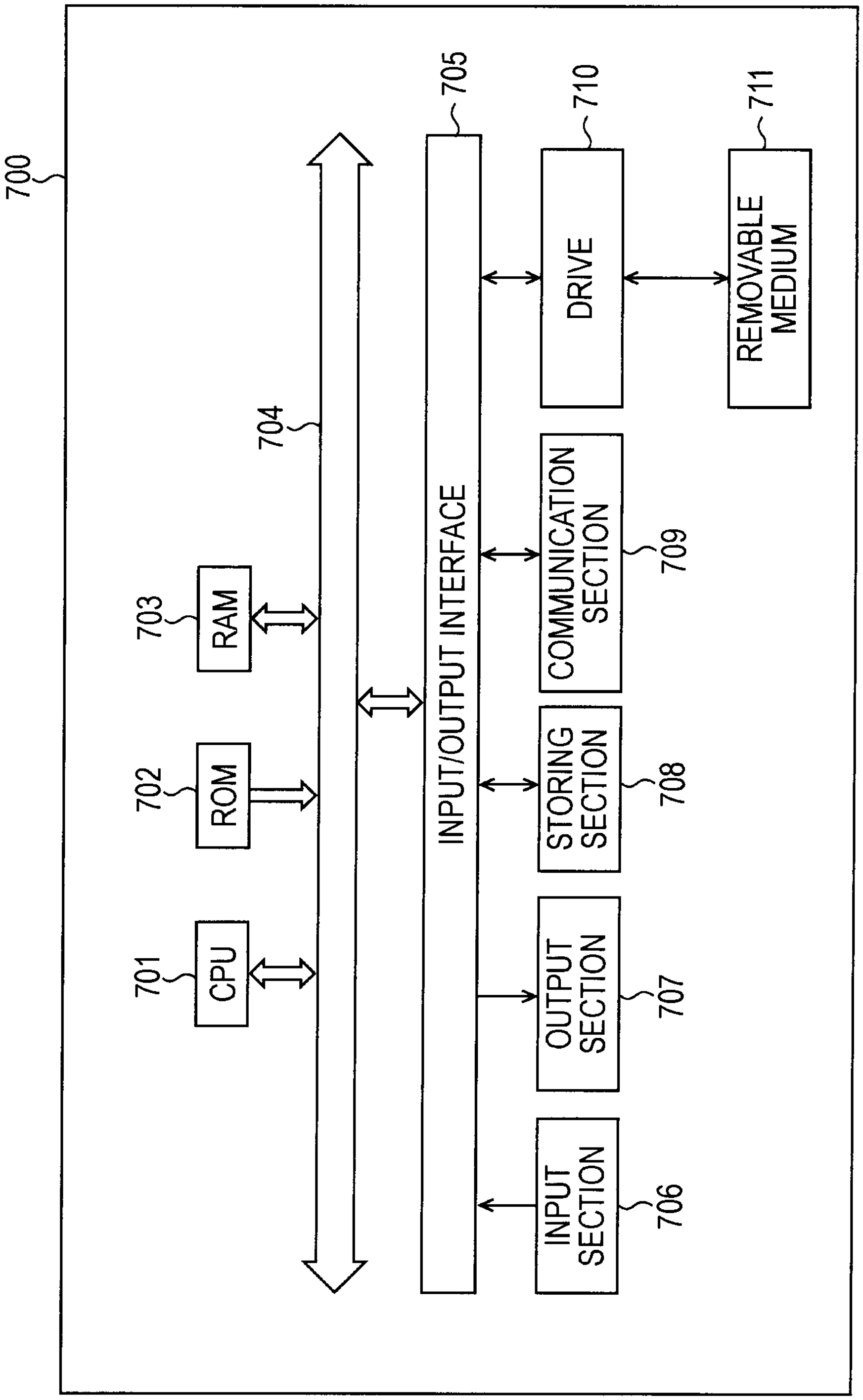
FIG. 11 is a block diagram showing an example of the configuration of a personal computer.

In FIG. 11, a CPU (Central Processing Unit) 701 executes various kinds of processing in accordance with a program stored in a ROM (Read Only Memory) 702, or a program loaded into a RAM (Random Access Memory) 703 from a storing section 708. The RAM 703 also stores data necessary for the CPU 701 to execute various kinds of processing, or the like as appropriate.

The CPU 701, the ROM 702, and the RAM 703 are connected to each other via a bus 704. The bus 704 is also connected with an input/output interface 705.

The input/output interface 705 is connected with an input section 706 formed by a keyboard, a mouse, or the like, and an output section 707 formed by a display such as an LCD (Liquid Crystal display), a speaker, or the like. Also, the input/output interface 705 is connected with the storing section 708 formed by a hard disk or the like, and a communication section 709 formed by a modem, a network interface card such as a LAN card, or the like. The communication section 709 performs communication processing via a network including the Internet.

The input/output interface 705 is also connected with a drive 710 as necessary, in which a removable medium 711 such as a magnetic disk, an optical disk, a magneto-optical disk, or a semiconductor memory is inserted as appropriate. A computer program read from those kinds of removable media is installed into the storing section 708 as necessary.

If the series of processes described above is to be executed by software, a program constituting the software is installed from a network such as the Internet, or a recording medium formed by the removable medium 711 or the like.

It should be noted that this recording medium includes not only a recording medium formed by the removal medium 711 such as a magnetic disk (including a floppy disk (registered trademark)), an optical disk (including a CD-ROM (Compact Disk-Read Only Memory) and a DVD (Digital Versatile Disk)), a magneto-optical disk (including an MD (Mini-Disk) (registered trademark)), or a semiconductor memory in which the program is recorded, which is distributed to the user to deliver the program separately from the apparatus body, but also a recording medium formed by the ROM 702, a hard disk included in the storing section 708, or the like in which the program is recorded, which is distributed to the user while being pre-embedded in the apparatus body.

It should be noted that the series of processes described above in this specification includes not only processes that are executed in a time-series fashion in the order as described, but may also include processes that are not necessarily executed in a time-series fashion but are executed in a parallel fashion or independently.

Also, embodiments of the present disclosure are not limited to the above-described embodiments, but various modifications are possible without departing from the scope of the present disclosure.

The present disclosure contains subject matter related to that disclosed in Japanese Priority Patent Application JP 2010-286369 filed in the Japan Patent Office on Dec. 22, 2010, the entire contents of which are hereby incorporated by reference.

What is claimed is:

1. A noise reduction apparatus, comprising:

a microphone that picks up a noise from surroundings of a casing;

a cancellation signal generating section that generates a cancellation signal for reducing the noise from surroundings, by applying filtering to a signal picked up by the microphone;

a predicted signal computing section that computes a predicted signal by predicting a noise from surroundings leaking into the casing, on a basis of the signal picked up by the microphone;

an additional-signal control section that generates an additional signal for improving a listening feel of an actual residual noise, wherein the additional signal is based on a predicted residual noise obtained by adding the cancellation signal and the predicted signal, wherein the actual residual noise is a result of the filtering of the signal picked up by the microphone; and an addition/output section that adds and outputs the additional signal and the cancellation signal.

2. The noise reduction apparatus according to claim 1, wherein the additional-signal control section includes a spectral shape computing section that computes a spectral shape of the predicted residual noise, by splitting the predicted residual noise into a plurality of bands of frequencies, and computing a power of each of the split bands, and an additional-signal generating section that generates the additional signal for correcting the computed spectral shape in accordance with a pre-set criterion.

3. The noise reduction apparatus according to claim 2, wherein:

the additional-signal control section further includes a storing section that stores one or a plurality of spectral shapes of sounds that cause relatively little discomfort to a human being, and a selecting section that selects one spectral shape from among the one or plurality of spectral shapes stored in the storing section, in accordance with the spectral shape computed by the spectral shape computing section; and the additional-signal generating section generates the additional signal that brings the spectral shape computed by the spectral shape computing section closer to the selected spectral shape.

4. A noise reduction method comprising:

picking up a noise from surroundings of a casing, by a microphone;

generating a cancellation signal for reducing the noise from surroundings, by applying filtering to a signal picked up by the microphone;

computing a predicted signal by predicting a noise from surroundings leaking into the casing, on a basis of the signal picked up by the microphone;

generating an additional signal for improving a listening feel of an actual residual noise, wherein the additional signal is based on a predicted residual noise obtained by adding the cancellation signal and the predicted signal, wherein the actual residual noise is a result of the filtering of the signal picked up by the microphone; and adding and outputting the additional signal and the cancellation signal.

5. A non-transitory computer-readable medium having embodied thereon a program, which when executed by a processor of a computer causes the processor to function as a noise reduction apparatus including:

a microphone that picks up a noise from surroundings of a casing;

a cancellation signal generating section that generates a cancellation signal for reducing the noise from surroundings, by applying filtering to a signal picked up by the microphone;

a predicted signal computing section that computes a predicted signal by predicting a noise from surroundings leaking into the casing, on a basis of the signal picked up by the microphone;

an additional-signal control section that generates an additional signal for improving a listening feel of an actual residual noise, wherein the additional signal is based on a predicted residual noise obtained by adding the cancellation signal and the predicted signal, wherein the actual residual noise is a result of the filtering of the signal picked up by the microphone; and an addition/output section that adds and outputs the additional signal and the cancellation signal.

* * * * *